(12) United States Patent
Green et al.

(10) Patent No.: US 9,991,106 B2
(45) Date of Patent: Jun. 5, 2018

(54) MASS SPECTROMETER WITH DIGITAL STEP ATTENUATOR

(71) Applicant: Micromass UK Limited, Wilmslow (GB)

(72) Inventors: Martin Raymond Green, Bowdon (GB); Steven Derek Pringle, Darwen (GB); Keith George Richardson, High Peak (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days. days.

(21) Appl. No.: 15/248,401

(22) Filed: Aug. 26, 2016

(65) Prior Publication Data

US 2017/0062197 A1 Mar. 2, 2017

(30) Foreign Application Priority Data

Aug. 28, 2015 (GB) .................................. 1515357.0

(51) Int. Cl.

| | | |
|---|---|---|
| *H01J 49/00* | (2006.01) | |
| *H01J 49/02* | (2006.01) | |
| *H01J 49/40* | (2006.01) | |
| *G01N 27/62* | (2006.01) | |

(52) U.S. Cl.
CPC ...... *H01J 49/0036* (2013.01); *H01J 49/0009* (2013.01); *H01J 49/022* (2013.01); *H01J 49/40* (2013.01); *G01N 27/622* (2013.01)

(58) Field of Classification Search
CPC ...... H01J 49/0036; H01J 49/40; H01J 49/022; H01J 49/0009; G01N 27/622

USPC ......................................... 250/281, 282, 287
See application file for complete search history.

(56) References Cited

U.S. PATENT DOCUMENTS

| | | | |
|---|---|---|---|
| 3,639,741 A | 2/1972 | Carrick | |
| 5,248,882 A | 9/1993 | Liang | |
| 5,926,124 A | 7/1999 | Shimomura | |
| 7,154,087 B2 | 12/2006 | Giannantonio et al. | |
| 7,238,936 B2 | 7/2007 | Okamura et al. | |
| 8,063,358 B2 | 11/2011 | Bateman et al. | |
| 8,354,634 B2 | 1/2013 | Green et al. | |
| 9,324,545 B2 * | 4/2016 | Green | H01J 49/0009 |
| 9,404,955 B2 * | 8/2016 | Green | G01R 29/26 |
| 9,711,337 B2 * | 7/2017 | Green | H01J 49/0036 |
| 2006/0054809 A1 | 3/2006 | Giannantonio et al. | |
| 2008/0073504 A1 * | 3/2008 | Shinbo | H01J 49/0036 250/287 |
| 2012/0119078 A1 * | 5/2012 | Green | H01J 49/4265 250/282 |
| 2015/0136971 A1 * | 5/2015 | Green | H01J 49/0009 250/282 |

FOREIGN PATENT DOCUMENTS

| | | | |
|---|---|---|---|
| GB | 1484742 | 9/1977 | |
| JP | 2000299084 | 10/2000 | |
| WO | 02/071027 | 9/2002 | |
| WO | WO 02071027 A2 * | 9/2002 | ......... H01J 49/0031 |

* cited by examiner

*Primary Examiner* — Michael Maskell (57) ABSTRACT

A method is disclosed comprising passing a signal output from a detector through a programmable attenuator or a programmable amplifier prior to digitizing the signal, and switching an attenuation factor or gain factor of the programmable attenuator or the programmable amplifier one or more times during a data acquisition period.

11 Claims, 3 Drawing Sheets

| Attenuation factor | [5] attenuation = 2 | [6] attenuation = 4 | [7] attenuation = 8 |
|---|---|---|---|
| 1 | | | |
| 2 | X | | |
| 4 | | X | |
| 6 | X | X | |
| 8 | | | X |
| 10 | X | | X |
| 12 | | X | X |

Fig. 3

MASS SPECTROMETER WITH DIGITAL STEP ATTENUATOR

CROSS-REFERENCE TO RELATED APPLICATION

This application claims priority from and the benefit of United Kingdom patent application No. 1515357.0 filed on 28 Aug. 2015. The entire content of this application is incorporated herein by reference.

FIELD OF THE INVENTION

The present invention relates generally to mass and/or ion mobility spectrometers and in particular to mass and/or ion mobility spectrometry detection systems.

BACKGROUND

It is known to record or digitise individual signals or transients arising from ion arrivals at an ion detector or an electron multiplier using an Analogue to Digital recorder or an Analogue to Digital Converter ("ADC"). Orthogonal acceleration Time of Flight mass spectrometers may digitise ion arrival signals or transients relating to many thousands of individual time of flight separations. The digitised signals or transients are summed to produce a final summed or composite time of flight mass spectrum. Each individual time of flight spectrum, signal or transient may be processed in real time before summing. In the simplest case this processing may be the application of an amplitude threshold to isolate signals arising from ion arrivals from background noise or baseline noise. The signal at individual digitised samples (i.e. individual Analogue to Digital Converter time bins) or within a time of flight spectrum which is above the threshold may be recorded and all other samples or intensity values in Analogue to Digital Converter time bins may be set to zero or to a baseline value. Multiple time of flight spectra processed in this way may then be summed or averaged to generate a final summed spectrum with reduced noise.

It is also known to process individual signals or transients which have been digitised to reduce the ion arrival signals or transients into time and intensity pairs. Such a method is disclosed, for example, in U.S. Pat. No. 8,063,358 (Micromass). Individual signals or transients which are reduced to time and intensity pairs may then be summed with other time and intensity pairs relating to other time of flight spectra, signals or transients in order to produce a final summed, composite or average spectrum. This method advantageously substantially removes the profile or line width of the digitised signal from the final summed spectra thereby increasing the effective time of flight resolution.

However, one particular problem with conventional Analogue to Digital Converter detection systems is that they can still suffer from a relatively limited dynamic range.

Arrangements are known which comprise dual Analogue to Digital Converters in an attempt to extend the dynamic range as is disclosed, for example, in U.S. Pat. No. 8,354,634 (Micromass).

It is desired to provide an improved method of mass and/or ion mobility spectrometry.

SUMMARY

According to an aspect, there is provided a method comprising:

passing a signal output from a detector through a programmable attenuator or a programmable amplifier prior to digitising the signal; and switching an attenuation factor or gain factor of the programmable attenuator or the programmable amplifier one or more times during a data acquisition period.

Various embodiments are directed to the use of a programmable attenuator, such as a high speed digital step attenuator ("DSA"), or a programmable amplifier, such as a high speed digital variable gain amplifier ("VGA"), to improve the dynamic range of a mass and/or ion mobility spectrometer detection system.

In operation the output from a mass and/or ion mobility spectrometer detection system may first be passed through a programmable attenuator or amplifier before optionally being passed through a secondary pre-amplification stage. The signal may then be passed to a digitiser to be digitised.

According to various embodiments the attenuator or amplifier may be switched one or more times during a data acquisition period, e.g. so as to reduce the intensity of the signal before the signal is then subsequently digitised in order to ensure that the signal does not exceed the dynamic range of the digitisation device.

It will be appreciated, therefore, that various embodiments provide an improved method of mass and/or ion mobility spectrometry.

The detector may comprise an ion detector, such as an electron multiplier or photo-multiplier ion detector.

The detector may comprise a chromatography detector, an ultra-violet ("UV") detector, a diode array detector, a thermal conductivity detector, a fluorescence detector, a flame ionization detector, a flame photometric detector, an atomic emission detector, an evaporative light scattering detector, an electron capture detector, a photo ionization detector or a refractive index detector.

The signal may comprise one or more ion signals, one or more time of flight transients or one or more ion mobility signals.

The data acquisition period may comprise the time to acquire a single time of flight transient or push and/or the time to perform a single ion mobility cycle.

The data acquisition period may comprise the time to acquire and sum multiple time of flight transients or pushes so as to form a mass spectrum and/or the time to perform multiple ion mobility cycles.

The attenuation or gain of the programmable attenuator or the programmable amplifier may be altered based upon whether the intensity of one or more ion peaks approaches or exceeds an intensity level and/or based upon a determined or predicted ion arrival rate and/or based upon a degree of saturation experienced by a digitiser and/or based upon how close a digitiser is to experiencing saturation effects.

The method may comprise rescaling the signal output from the programmable attenuator or the programmable amplifier or a signal derived from the signal output from the programmable attenuator or the programmable amplifier dependent upon how the attenuation factor or the gain factor was varied during the course of the data acquisition period.

The method may comprise repeatedly switching the attenuation factor or gain factor of the programmable attenuator or the programmable amplifier between two or more pre-set attenuation or gain factors during the data acquisition period.

The method may comprise:

acquiring a first data set at a first attenuation or gain factor;

acquiring a second data set at a second different attenuation or gain factor; and combining one or more portions of the first data set with one or more portions of the second data set so as to form a composite or combined data set.

The programmable attenuator or programmable amplifier may be arranged to have a constant signal propagation delay time when operating at a plurality of different attenuation factors or gain factors.

The method may comprise determining one or more signal propagation delay times when the programmable attenuator or the programmable amplifier is arranged to operate at one or more different attenuation factors or gain factors.

The method may comprise correcting a signal output from the programmable attenuator or the programmable amplifier or derived from a signal output from the programmable attenuator or the programmable amplifier so as to correct for one or more determined signal propagation delay times.

The method may comprise correcting a time to mass or a time to mass to charge ratio calibration dependent upon an attenuation factor or gain factor of the programmable attenuator or the programmable amplifier.

According to an aspect, there is provided a method of time of flight mass spectrometry, comprising the method as described above.

According to an aspect there is provided a spectrometer comprising:
a detector;
a programmable attenuator or a programmable amplifier arranged to receive a signal output from the detector; and
a digitiser arranged and adapted to digitise a signal output from the programmable attenuator or the programmable amplifier; wherein the spectrometer is configured:
to switch an attenuation factor or gain factor of the programmable attenuator or the programmable amplifier one or more times during a data acquisition period.

The spectrometer may comprise a time of flight mass spectrometer.

According to an aspect there is provided a method of mass spectrometry comprising:
passing a signal output from a detector through a programmable attenuator or a programmable amplifier prior to digitising the signal.

Various embodiments relate to the use of a high speed digital step attenuator ("DSA") or a high speed digital variable gain amplifier ("VGA") to improve the dynamic range of a mass spectrometer detection system.

In operation the output from a mass spectrometer detection system may first be passed through a programmable attenuator or amplifier before optionally being passed through a secondary pre-amplification stage. The signal may then be passed to a digitiser to be recorded.

According to various embodiments the attenuator or amplifier may be programmed to reduce the intensity of the signal before the signal is then subsequently digitised in order to ensure that the signal does not exceed the dynamic range of the digitisation device.

The programmable attenuator or amplifier may be arranged to reduce or increase the intensity of the signal.

The various embodiments extend the dynamic range of measurements using an ADC by attenuating the signal before or prior to digitisation.

The speed at which attenuation may be changed allows manipulation of the signal intensity during very fast separations or other fast processes. Existing methods which employ alteration of the ion beam transmission are often too slow to keep up with these processes.

In addition the digital step attenuator provides a deterministic, reproducible attenuation and is not susceptible to surface charging effects which can cause errors when using electrostatic lenses to alter the ion transmission.

Correction for propagation time delays with the digital step attenuator are disclosed herewith allowing operation with high resolution Time of Flight mass spectrometers.

The programmable attenuator or amplifier may comprise a digital step attenuator ("DSA").

The programmable attenuator or amplifier may comprise a variable gain amplifier ("VGA").

The detector may comprise an ion detector.

The detector may comprise a chromatography detector, an ultra-violet ("UV") detector, a diode array detector, a thermal conductivity detector, a fluorescence detector, a flame ionization detector, a flame photometric detector, an atomic emission detector, an evaporative light scattering detector, an electron capture detector, a photo ionization detector or a refractive index detector.

The detector may comprise a destructive chromatography detector.

The destructive chromatography detector may be selected from the group consisting of: (i) a Flame Ionization Detector ("FID"); (ii) an aerosol-based detector or Nano Quantity Analyte Detector ("NQAD"); (iii) a Flame Photometric Detector ("FPD"); (iv) an Atomic Emission Detector ("AED"); (v) a Nitrogen Phosphorus Detector ("NPD"); and (vi) an Evaporative Light Scattering Detector ("ELSD").

The detector may comprise a non-destructive chromatography detector.

The non-destructive chromatography detector may be selected from the group consisting of: (i) a fixed or variable wavelength UV detector; (ii) a Thermal Conductivity Detector ("TCD"); (iii) a fluorescence detector; (iv) an Electron Capture Detector ("ECD"); (v) a conductivity monitor, (vi) a Photoionization Detector ("PID"); (vii) a Refractive Index Detector ("RID"); (viii) a radio flow detector; and (ix) a chiral detector.

The signal may comprise one or more ion signals, one or more time of flight transients or one or more ion mobility signals.

The method may further comprise switching an attenuation factor or gain factor of the programmable attenuator or the programmable amplifier one or more times during a single data acquisition period.

The data acquisition period may comprise the time to acquire either a single time of flight transient or the time to perform a single ion mobility cycle.

The method may further comprise recording how the attenuation factor or the gain factor is varied during the course of the single data acquisition period.

The method may further comprise rescaling the signal output from the programmable attenuator or the programmable amplifier or a signal derived from the signal output from the programmable attenuator or the programmable amplifier dependent upon how the attenuation factor or the gain factor was varied during the course of the single data acquisition period.

The method may further comprise switching an attenuation factor or gain factor of the programmable attenuator or the programmable amplifier one or more times during an extended data acquisition period.

The extended data acquisition period may comprise the time to acquire and sum multiple time of flight transients so as to form a mass spectrum or the time to perform multiple ion mobility cycles.

The method may further comprise recording how the attenuation factor or the gain factor is varied during the course of the extended data acquisition period.

The method may further comprise rescaling the signal output from the programmable attenuator or the programmable amplifier or a signal derived from the signal output from the programmable attenuator or the programmable amplifier dependent upon how the attenuation factor or the gain factor is varied during the course of the extended data acquisition period.

The method may further comprise acquiring a first data set at a first attenuation or gain factor during a first data acquisition period and acquiring a second data set at a second different attenuation or gain factor during the same first data acquisition period.

The method may further comprise acquiring a first data set at a first attenuation or gain factor during a first data acquisition period and acquiring a second data set at a second different attenuation or gain factor during a subsequent second data acquisition period.

The method may further comprise combining one or more portions of the first data set with one or more portions of the second data set so as to form a composite or combined data set.

The method may further comprise rescaling a signal output from the programmable attenuator or the programmable amplifier and/or rescaling data values derived from a signal output from the programmable attenuator or the programmable amplifier.

The method may further comprise altering the attenuation or gain of the programmable attenuator or the programmable amplifier one or more times before and/or during and/or after one or more data acquisition periods.

The attenuation or gain of the programmable attenuator or the programmable amplifier may be altered based upon whether or not the intensity of one or more ion peaks approaches or exceeds an intensity level and/or based upon a determined or predicted ion arrival rate and/or based upon a degree of saturation experienced by a digitiser and/or based upon how close a digitiser is to experiencing saturation effects.

The method may further comprise digitising a signal output from the programmable attenuator or the programmable amplifier using one or more Analogue to Digital Converters ("ADCs").

The method may further comprise using a test signal and/or calibration data to ensure or check the accuracy of an attenuation factor or gain factor of the programmable attenuator or the programmable amplifier.

The method may further comprise pre-calibrating the programmable attenuator or the programmable amplifier to determine one or more signal propagation delay times when the programmable attenuator or the programmable amplifier is arranged to operate at one or more different attenuation factors or gain factors.

The programmable attenuator or programmable amplifier may be arranged to have a constant signal propagation delay time when operating at a plurality of different attenuation factors or gain factors.

The method may further comprise correcting a signal output from the programmable attenuator or the programmable amplifier or derived from a signal output from the programmable attenuator or the programmable amplifier so as to correct for the determined signal propagation delay times.

The method may further comprise correcting a time to mass or a time to mass to charge ratio calibration dependent upon an attenuation factor or gain factor of the programmable attenuator or the programmable amplifier.

The method may further comprise varying an attenuation factor and/or the transmission of an ion-optical device.

The ion-optical device may comprise a mass filter, an ion trap, an ion gate, an ion lens, an ion guide, an electrode or an ion beam attenuator.

Embodiments are contemplated wherein the attenuation factor may be varied whilst an instrument parameter is scanning, stepping or changing optionally in reaction to the intensity at the detector varying. For example, a quadrupole set mass scan, an ion trap mass selective ejection scan or an ion mobility separation may be performed. An attenuator may be used in conjunction with a dynamically varying or changing ion population.

According to another aspect there is provided a mass spectrometer comprising:

a detector;

a programmable attenuator or a programmable amplifier arranged to receive a signal output from the detector; and a digitiser arranged and adapted to digitise a signal output from the programmable attenuator or the programmable amplifier.

According to an aspect there is provided a method of chromatography analysis or ion mobility separation comprising:

passing a signal output from a detector through a programmable attenuator or a programmable amplifier prior to digitising the signal.

According to an aspect there is provided a chromatographic analyser or ion mobility separator comprising:

a detector;

a programmable attenuator or a programmable amplifier arranged to receive a signal output from the detector; and a digitiser arranged and adapted to digitise a signal output from the programmable attenuator or the programmable amplifier.

According to an aspect there is provided a method of increasing the dynamic range of a spectrometer comprising:

providing an analogue signal corresponding to analyte arriving at a detector;

providing a digitization device to digitize said analogue signal;

providing a digitally programmable attenuator or amplifier downstream of the detector and upstream of the digitisation device, wherein the digitally programmable attenuation or amplification device is programmed: (i) to alter the attenuation or amplification value applied to the analogue signal based on interrogation of recorded data such that all the analogue signals or specific predetermined analogue signals are maintained within the dynamic range of the digitization device; or (ii) to switch between two or more preset attenuation or amplification values repetitively and sequentially for part of or all of the analysis time; and wherein the attenuated digitized data is rescaled based on the applied attenuation or amplification factor.

The spectrometer may comprise a mass spectrometer.

The spectrometer may contain an ion mobility separator.

The spectrometer may be calibrated in mass to charge ratio and/or attenuation value at each attenuation level and the digitized attenuated data may be adjusted based on this calibration.

The spectrometer may comprise an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") on source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") on source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; (xxviii) a Laser Ablation Electrospray Ionisation ("LAESI") ion source; and (xxix) Surface Assisted Laser Desorption Ionisation ("SALDI").

The spectrometer may comprise one or more continuous or pulsed ion sources.

The spectrometer may comprise one or more ion guides.

The spectrometer may comprise one or more ion mobility separation devices and/or one or more Field Asymmetric Ion Mobility Spectrometer devices.

The spectrometer may comprise one or more ion traps or one or more ion trapping regions.

The spectrometer may comprise one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

The ion-molecule reaction device may be configured to perform ozonlysis for the location of olefinic (double) bonds in lipids.

The spectrometer may comprise a mass analyser selected from the group consisting of: (i) a quadrupole mass analyser; (ii) a 2D or linear quadrupole mass analyser (iii) a Paul or 3D quadrupole mass analyser, (iv) a Penning trap mass analyser; (v) an ion trap mass analyser; (vi) a magnetic sector mass analyser; (vii) Ion Cyclotron Resonance ("ICR") mass analyser, (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser (xiii) an orthogonal acceleration Time of Flight mass analyser and (xiv) a linear acceleration Time of Flight mass analyser.

The spectrometer may comprise one or more energy analysers or electrostatic energy analysers.

The spectrometer may comprise one or more ion detectors.

The spectrometer may comprise one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter.

The spectrometer may comprise a device or ion gate for pulsing ions; and/or a device for converting a substantially continuous ion beam into a pulsed ion beam.

The spectrometer may comprise a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser.

The spectrometer may comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) > about 500 V peak to peak.

The AC or RF voltage may have a frequency selected from the group consisting of: (i) < about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) > about 10.0 MHz.

The spectrometer may comprise a chromatography or other separation device upstream of an ion source. The chromatography separation device may comprise a liquid chromatography or gas chromatography device. Alternatively, the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) < about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar and (ix) > about 1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

A chromatography detector may be provided, wherein the chromatography detector comprises either:

a destructive chromatography detector optionally selected from the group consisting of (i) a Flame Ionization Detector (FID); (ii) an aerosol-based detector or Nano Quantity Analyte Detector (NQAD); (iii) a Flame Photometric Detector (FPD); (iv) an Atomic-Emission Detector (AED); (v) a Nitrogen Phosphorus Detector (NPD); and (vi) an Evaporative Ught Scattering Detector (ELSD); or a non-destructive chromatography detector optionally selected from the group consisting of: (i) a fixed or variable wavelength UV detector; (ii) a Thermal Conductivity Detector (TCD); (ii) a fluorescence detector; (iv) an Electron Capture Detector (ECD); (v) a conductivity monitor; (vi) a Photoionization Detector (PID); (vii) a Refractive Index Detector (RID); (viii) a radio flow detector; and (ix) a chiral detector.

The spectrometer may be operated in various modes of operation including a mass spectrometry ("MS") mode of operation; a tandem mass spectrometry ("MS/MS") mode of operation; a mode of operation in which parent or precursor ions are alternatively fragmented or reacted so as to produce fragment or product Ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation a Quantification mode of operation or an Ion Mobility Spectrometry ("IMS") mode of operation.

BRIEF DESCRIPTION OF THE DRAWINGS

Various embodiments will now be described, by way of example only, and with reference to the accompanying drawings in which.

DETAILED DESCRIPTION

Various embodiments are directed to a method in which a signal output from a detector is passed through a programmable attenuator or a programmable amplifier before the signal is digitised. An attenuation factor or gain factor of the programmable attenuator or the programmable amplifier is switched one or more times during a data acquisition period.

Figure 1:
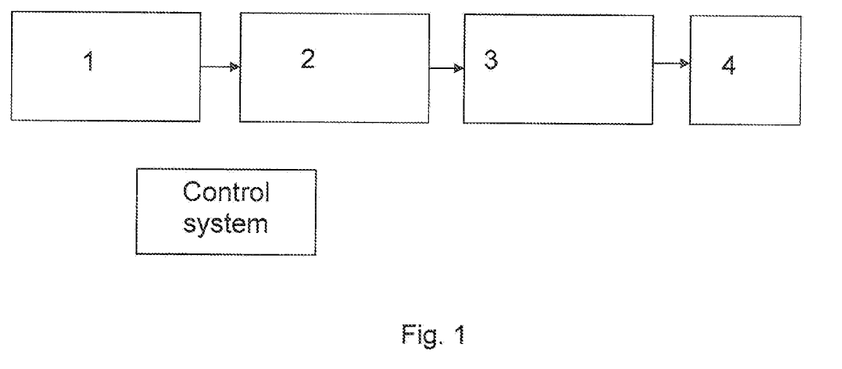
FIG. 1 shows an embodiment comprising an analytical device, a detector, a digital step attenuator or a digital variable gain amplifier which attenuates or amplifies a signal output from the detector and an Analogue to Digital Converter which digitises the attenuated or amplified signal output from the digital step attenuator or the digital variable gain amplifier.

FIG. 1 shows an embodiment comprising an analytical device 1 such as an ion separator or filter, a detector 2 which outputs a signal, a digital step attenuator or a digital variable gain amplifier 3 which is arranged to attenuate or amplify the signal output from the detector 2 and an Analogue to Digital Converter ("ADC") 4 which is arranged to digitise the attenuated or amplified signal output from the digital step attenuator or digital variable gain amplifier 3.

The analytical device 1 may comprise a mass spectrometer and/or an ion mobility separator device. According to various embodiments, the analytical device 1 may comprise a mass spectrometer downstream of an ion mobility separator. The mass spectrometer may, for example, comprise a quadrupole mass filter, an analytical ion trap or a Time of Flight mass analyser (or combinations of these devices).

The detector 2 may comprise an ion detector, such as an electron multiplier or photo-multiplier ion detector, e.g. that is part of a mass and/or ion mobility spectrometer. However, according to other embodiments the detector 2 may comprise a chromatography detector such as an ultra-violet ("UV") detector, a diode array detector, a thermal conductivity detector, a fluorescence detector, a flame ionization detector, a flame photometric detector, an atomic emission detector, an evaporative light scattering detector, an electron capture detector, a photo ionization detector or a refractive index detector.

Signals produced or otherwise output by the detector 2 (with or without pre-amplification) are passed through a digital step attenuator ("DSA") or a digital variable gain amplifier ("VGA") 3. In general, a digital variable gain amplifier 3 incorporates a gain stage integrated with a digital step attenuator to allow the overall gain to be varied.

A digital step attenuator 3 comprises a device for which a known amount of attenuation may be selected at high speed by application of a suitable signal. Digital step attenuator devices switch in discrete finite attenuation states.

Many different digital step attenuator devices are commercially available having a wide bandwidth and having various different driver and control technologies. Semiconductor devices such as GaAs MESFETs, PIN Diodes or MOSFETs can achieve switching times approaching solid state switches.

Figure 2:
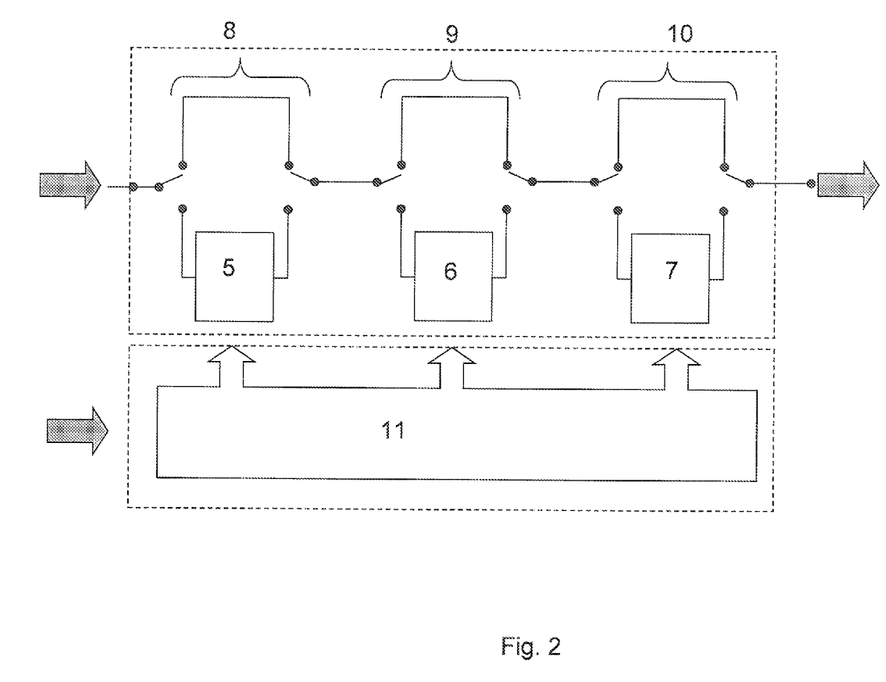
FIG. 2 shows a three bit digital step attenuator according to an embodiment.

FIG. 2 shows a schematic representation of a three bit digital step attenuator 3 according to an embodiment which comprises three attenuation stages 5,6,7. The digital step attenuator 3 comprises three switches 8,9,10 operated by a control signal and driver module 11. The device as shown in FIG. 2 is shown being operated in non-attenuating mode of operation wherein none of the attenuation stages 5,6,7 affect the signal path and hence wherein a signal is not attenuated by the attenuator 3.

For the purposes of illustration only a first attenuation stage 5 may be considered which is arranged to attenuate a signal by a factor of x2. The first attenuation stage 5 is followed by a second attenuation stage 6 which is arranged to attenuate the signal by a factor of x4. The second attenuation stage 6 is followed by a third attenuation stage 7 which is arranged to attenuate the signal by a factor of x8. Accordingly, eight states are accessible by suitably programming the three switches 5,6,7.

Figure 3:
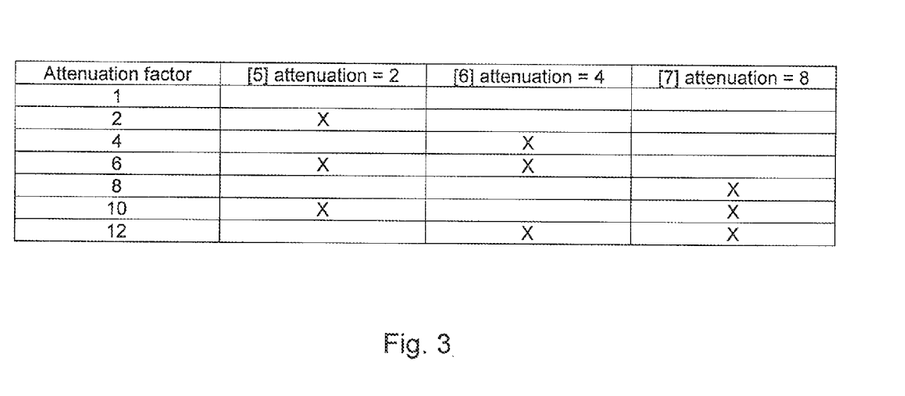
FIG. 3 shows a table illustrating the state of each switch in the three bit digital step attenuator shown in FIG. 2.

FIG. 3 shows a table illustrating the state of each of the three switches 5,6,7 shown in FIG. 2 which enables eight different attenuation values to be produced according to an illustrative example. It will be apparent that if more switches are provided, then a greater number of attenuation states can then be accessed and a finer control of the attenuation of the signal can be achieved.

Several different types of digital step attenuator devices are commercially available from several different manufacturers. For example, one suitable device is a Peregrine Semiconductor PE43703 7-bit RF digital step attenuator. This device allows 7 bit digital control of the signal attenuation value with as fine as 0.25 dB steps, up to an attenuation factor of 31.75 dB. This is a maximum 38.7 times attenuation with up to 128 discrete programmable attenuation values. This particular device has a bandwidth of 9 kHz to 4 GHz and a switching time of 650 ns with a rise and fall time of 400 ns. The device has a maximum switching frequency of 25 kHz and has a maximum input power of 23 dBm or 23 dBmW (200 mW). The very rapid switching and settling time of this device makes it ideal for mass spectrometry applications.

It will, however, be understood that other digital step attenuator devices may be used which may have different or slightly different characteristics.

An Analogue to Digital Converter ("ADC") 4 is arranged to digitise the attenuated or amplified signal output from the digital step attenuator or digital variable gain amplifier 3.

As also shown in FIG. 1, according to various embodiments, a control system may be provided. The control system may be separate from or integral with the digital step attenuator or digital variable gain amplifier 3 and/or the Analogue to Digital Converter ("ADC") 4, or otherwise. The control system may be configured to control the operation of the spectrometer, e.g. in the manner of the various embodiments described herein. The control system may comprise suitable control circuitry that is configured to cause the spectrometer to operate in the manner of the various embodiments described herein. The control system may also comprise suitable processing circuitry configured to perform any one or more or all of the necessary processing and/or post-processing operations in respect of the various embodiments described herein.

The digital step attenuator 3 may be used in a feedback or a data dependent mode. For example, the attenuation factor of the digital step attenuator 3 may be switched based on the value of the signal output from the detector, or based on a predicted value of the signal output from the detector, e.g.

relative to one or more threshold values, such that saturation effects are reduced or avoided.

According to various other embodiments the digital step attenuator 3 may be switched repetitively or repeatedly between two or more pre-set values, e.g. without regard to the value of the signal output from the detector, and the resulting data may be combined to give a composite spectrum. In this case, where saturated and/or distorted data is present in a data set acquired using a lower attenuation factor, it may be replaced or combined with (suitably scaled) corresponding data acquired using a larger attenuation factor, e.g. so as to provide a composite data set having a relatively increased dynamic range.

Various different operational modes of the digital step attenuator 3 are discussed in more detail below.

Feedback Attenuation Control of Multiple Attenuation Values within an IMS Separation Cycle Combining ion mobility separation with orthogonal acceleration Time of Flight mass spectrometry results in significant challenges to downstream data recording electronics. Generally for orthogonally acceleration Time of Flight instruments a mass spectrum is constructed from summation of many individual time of flight transients. Each individual time of flight transient is recorded with limited dynamic range generally using an Analogue to Digital recorder (ADC). However, the overall detection dynamic range is increased by summing multiple transients.

An ion mobility separator with an overall cycle time of 10-20 ms can deliver ions arising from a single species in approximately 0.5-1 ms in each cycle thereby reducing the number of summed time of flight transients by 10-40 times and hence limiting the overall dynamic range of the summed data.

Various embodiments disclosed herein may be used to extend the dynamic range of this type of system by controlling the intensity of the digitised signal.

For example, a digital step attenuator 3 may be programmed to change between several attenuation values during an individual ion mobility separation cycle. In other words, the attenuation factor of the programmable attenuator may be switched one or more times during a data acquisition period comprising an individual ion mobility separation cycle.

In this way target ions at specific mass to charge ratios and/or ion mobility drift time values may be attenuated differently so that the signal produced does not exceed the dynamic range of the ADC.

For non-targeted analysis the base peak intensity may controlled as the ions elute from the ion mobility separator device. The fast switching time of the digital step attenuator 3 is well suited to this application.

A record of the attenuation factor used at each drift time may be used to rescale the data to maintain quantitative performance. Feedback control may be based on examination of an acquired IMS or IMS/MS spectrum from a previous scan or a pre-scan or based on a separate measure of ion current using a second detector.

Feedback Control Between or within a Time of Flight Transient

For orthogonal acceleration Time of Flight mass spectrometers typical flight times are in the order of 30-200 μs. Folded geometry, high resolution systems with much longer flight times (e.g. 1 ms and over) are also commercially available. The fast switching times of digital step attenuators allows switching of attenuation values between time of flight spectra.

Attenuation may be altered during summation of time of flight transients or pushes, e.g. based on the ion arrival rate or amount of digitiser saturation for a base peak intensity ("BPI") or a specific target ion region. Data from each time of flight transient or push may be rescaled optionally based on the known attenuation factor before it is added to a histogram to maintain quantification integrity.

In other words, the attenuation factor of the programmable attenuator may be switched one or more times during a data acquisition period comprising multiple time of flight transients or pushes. For example, the attenuation factor of the programmable attenuator may be switched between each time of flight transient or push.

Alternatively, the attenuation value may be switched within a single time of flight transient or push, e.g. to ensure one or more target signals or one or more base peaks within multiple regions are maintained within the dynamic range of the ADC.

That is, the attenuation factor of the programmable attenuator may be switched one or more times during a data acquisition period comprising a single time of flight transient or push.

Feedback Between Histogrammed or Combined MS or IMS-MS Spectra

According to various embodiments the digital step attenuator 3 may be switched in the period between each time allowed for summation of individual time of flight transients into a spectrum. That is, the attenuation factor of the programmable attenuator may be switched one or more times during a data acquisition period comprising the time for acquiring plural spectra. For example, the attenuation factor of the programmable attenuator may be switched between each spectrum or between each group of plural consecutive spectra. The attenuation value may be constant within each time of flight transient or push and within each summation period (spectrum).

For example, the digital step attenuator 3 may be programmed based upon the results of real-time processing of a previous spectrum or a combination of a number of spectra. According to various embodiments, the target may be to keep the total ion current ("TIC") within a given range or alternatively the target may be to keep the base peak intensity ("BPI") within a given mass to charge ratio and/or mobility range. In the case of an ion mobility separation experiment, either the spectra obtained from the current ion mobility separation or from previous ion mobility separations may be utilised.

Feedback Between Each Individual IMS Separation

Each ion mobility separation cycle may be between 10-20 ms in duration and data from several ion mobility separation cycles may be summed to present a final ion mobility separation. In various embodiments the attenuation factor may be adjusted between each on mobility separation cycle, e.g. during the period in which data from multiple ion mobility separations are summed.

That is, the attenuation factor of the programmable attenuator may be switched one or more times during a data acquisition period comprising plural ion mobility separation cycles. For example, the attenuation factor of the programmable attenuator may be switched between each ion mobility separation cycle.

Based upon the intensity within the previous separation, new attenuation values (increased or decreased) may be applied during the subsequent separation time.

The techniques according to various embodiments may be used when acquiring nested ion mobility-time of flight ("IMS-ToF") data sets. For example, attenuation factor of the programmable attenuator may be switched between each ion mobility separation cycle.

Attenuation Switching

According to various embodiments two or more fixed attenuation values may be chosen and the values may be alternated: (a) between each time of flight transient or push; (b) within each time of flight transient or push; (c) within each ion mobility separation time; (d) between each ion mobility separation; and (e) between each MS or IMS-MS summed spectral times.

In other words, the attenuation factor or gain factor of the programmable attenuator or the programmable amplifier may be repeatedly switched between two or more pre-set attenuation or gain factors during a data acquisition period. The attenuation factor or gain factor may be switched at pre-determined times or intervals during the data acquisition period.

The techniques according to various embodiments may be used when acquiring Time of Flight ("ToF") or nested ion mobility-time of flight ("IMS-ToF") data sets. For example, attenuation factor of the programmable attenuator may be switched between each ToF spectrum and/or between each ion mobility separation cycle.

In these embodiments, the two data streams may be combined into a composite high dynamic range data set, either during an acquisition or as a post-processing operation, resulting in an increase in overall dynamic range.

Data Dependent Attenuation Switching

According to various embodiments a mode of operation may be utilised wherein the signal or spectra may be monitored and the attenuation switching mode of operation as described above may be entered only if a target peak or a base peak has exceeded or approaches a specific intensity value or has saturated the digitiser.

The feedback attenuation modes of operation may also be applied to mass filters or mass filters in combination with Time of Flight systems, e.g. to ensure that the digitiser is not saturated for individual MRM channels of a tandem quadrupole mass spectrometer.

Various embodiments are also applicable to non-targeted acquisition modes, e.g. wherein a quadrupole mass filter is scanned or stepped with relatively low mass resolution or wide mass to charge ratio transmission characteristics and many separate time of flight mass spectra are acquired during this scan. This produces a nested quadrupole mass to charge ratio, time of flight mass to charge ratio data set. Ions exiting the quadrupole may be activated or fragmented to produce characteristic product ions which are then recorded by the Time of Flight mass spectrometer. Product ions recorded by the Time of Flight mass spectrometer may be associated with parent or precursor ion ranges related to the set mass of the quadrupole mass filter at different times during the quadrupole scan. In this way MS-MS spectra may be produced for all ions within the sample, albeit with low duty cycle. Modes of operation previously described may be performed, e.g. in which the attenuation factor may be varied within or between quadrupole mass filter scans in order to maintain the signal intensity of peaks within the dynamic range of the Time of Flight detection system.

A similar high duty cycle experiment may be performed using an analytical ion trap. In this case Ions may be mass selectively scanned out of the ion trap and parent or precursor ions and/or product ions may be recorded using a Time of Flight mass analyser. Fast variable attenuation may be used to maintain signal intensity within the dynamic range of the detection system during this experiment.

Calibration

Although the attenuation values are reproducible, it may be necessary or desirable to calibrate the digital step attenuator 3, e.g. using a test signal or calibration data, to ensure that intensity correction factors at each attenuation value are as accurate as possible.

When using a digital step attenuator 3 in combination with a Time of Flight mass analyser it is recognised that there may be a signal time delay associated with each attenuation value as different electronic components are switched in and out of the signal path. The resulting time delay may be different for each attenuation value and may be significant (e.g. of the order of tens of nano-seconds) so that if not corrected it could adversely affect mass accuracy.

It is recognised that when using a digital step attenuator 3 according to various embodiments where time is measured as well as intensity, the delay or time offset introduced at each of the attenuation levels may be determined during a pre-calibration step and compensated for or corrected in the acquired data. As such, calibration and correction for signal propagation delays through the attenuation device may be performed.

The dominant effect on the measured ion arrival time will be a time offset which may be slightly different at each attenuation value. One way of calibrating the digital step attenuator 3 is to provide a test signal which can be measured under each attenuation value. Determined time offsets may be stored in a look-up table and then used to correct the time to mass calibration of the spectrometer depending on the attenuation value.

Alternatively, a mass spectral calibrant compound may be analysed and the time offsets may be determined from the spectra produced.

According to various embodiments, it may only be necessary to determine the relative difference in the propagation delay between each attenuation value, and to then calibrate the spectrometer at a single attenuation value. Mass calibration would normally be performed with an attenuation factor of 1 where all the attenuation stages are bypassed. The propagation time offset value for the initial calibration may then be adjusted for data at other attenuation values.

Alternatively, the digital step attenuator or amplifier may be designed to have a constant propagation delay regardless of the attenuation level selected. This method negates the requirement for calibration of data for each attenuation value, after the data has been recorded.

Referring to FIG. 2, the time that the signal takes to pass through each switch 8,9,10 in the bypass state shown may be matched to the time taken for the signal to pass through the corresponding attenuation device 5,6,7 when the respective switch is in a position where the attenuation device is in the signal path.

One way to achieve this is to select the length of the cable between the poles of each switch when in the bypass position, as shown in FIG. 2, such that the propagation delay is identical to the delay when the switch is in the position where the corresponding attenuation device is in the signal path. Other methods of introducing a delay in these signal paths may be contemplated.

The effect of matching signal transit times for each attenuation device is to ensure that the overall propagation delay of the programmable attenuator is identical regardless of the attenuation value specified and the signal path programmed.

Although various embodiments have been described above primarily in terms of the use of a digital step attenuator, the various embodiments may alternatively be implanted using a programmable amplifier.

Although the present invention has been described with reference to preferred embodiments, it will be understood by those skilled in the art that various changes in form and detail may be made without departing from the scope of the invention as set forth in the accompanying claims.

The invention claimed is:

1. A method comprising:
passing a signal output from a detector through a programmable attenuator or a programmable amplifier prior to digitising said signal; and
switching an attenuation factor or gain factor of said programmable attenuator or said programmable amplifier one or more times during a data acquisition period;
wherein said programmable attenuator or programmable amplifier is arranged to have a constant signal propagation delay time when operating at a plurality of different attenuation factors or gain factors.

2. A method as claimed in claim 1, wherein said detector comprises an ion detector.

3. A method as claimed in claim 1, wherein said detector comprises a chromatography detector, an ultra-violet ("UV") detector, a diode array detector, a thermal conductivity detector, a fluorescence detector, a flame ionization detector, a flame photometric detector, an atomic emission detector, an evaporative light scattering detector, an electron capture detector, a photo ionization detector or a refractive index detector.

4. A method as claimed in claim 1, wherein said signal comprises one or more ion signals, one or more time of flight transients or one or more ion mobility signals.

5. A method as claimed in claim 1, wherein said data acquisition period comprises the time to acquire a single time of flight transient or push and/or the time to perform a single ion mobility cycle.

6. A method as claimed in claim 1, wherein said data acquisition period comprises the time to acquire and sum multiple time of flight transients or pushes so as to form a mass spectrum and/or the time to perform multiple ion mobility cycles.

7. A method as claimed in claim 1, wherein said attenuation or gain of said programmable attenuator or said programmable amplifier is altered based upon whether the intensity of one or more ion peaks approaches or exceeds an intensity level and/or based upon a determined or predicted ion arrival rate and/or based upon a degree of saturation experienced by a digitiser and/or based upon how close a digitiser is to experiencing saturation effects.

8. A method as claimed in claim 1, further comprising rescaling the signal output from said programmable attenuator or said programmable amplifier or a signal derived from the signal output from said programmable attenuator or said programmable amplifier dependent upon how said attenuation factor or said gain factor was varied during the course of said data acquisition period.

9. A method as claimed in claim 1, comprising repeatedly switching said attenuation factor or gain factor of said programmable attenuator or said programmable amplifier between two or more pre-set attenuation or gain factors during said data acquisition period.

10. A method as claimed in claim 1, further comprising:
acquiring a first data set at a first attenuation or gain factor;
acquiring a second data set at a second different attenuation or gain factor; and
combining one or more portions of said first data set with one or more portions of said second data set so as to form a composite or combined data set.

11. A spectrometer comprising:
a detector;
a programmable attenuator or a programmable amplifier arranged to receive a signal output from said detector; and
a digitiser arranged and adapted to digitise a signal output from said programmable attenuator or said programmable amplifier;
wherein said spectrometer is configured
to switch an attenuation factor or gain factor of said programmable attenuator or said programmable amplifier one or more times during a data acquisition period; and
wherein said programmable attenuator or programmable amplifier is arranged to have a constant signal propagation delay time when operating at a plurality of different attenuation factors or gain factors.

* * * * *